United States Patent [19]
Dobrenz et al.

[11] Patent Number: 6,005,165
[45] Date of Patent: Dec. 21, 1999

[54] SALT TOLERANT ALFALFA

[75] Inventors: Albert K. Dobrenz, deceased, late of Tucson; by Matthew Dobrenz, personal representative, Phoenix, both of Ariz.

[73] Assignee: Agripro Seeds, Inc., Shawnee Mission, Kans.

[21] Appl. No.: 08/874,894

[22] Filed: Jun. 13, 1997

[51] Int. Cl.$^6$ .............................. A01H 5/00; A01H 5/10
[52] U.S. Cl. .............................................. 800/260; 800/298
[58] Field of Search ..................................... 800/260, 265, 800/298

[56] References Cited

U.S. PATENT DOCUMENTS 4,616,100  10/1986  McHughen ............................. 800/298

OTHER PUBLICATIONS

Dobrenz, A.K.; Robinson, D.L.; Smith, S.E.; and D.C. Poteet, Corp Sci. 29:493, 1989.
Johnson, D.W.; Smith, S.E.; and A.K. Dobrenz, Corp Sci., 31:1098–1099, 1991.
Allen, S.G.; Dobrenz, A.K.; Schonhorst, M.H.; and J.E. Stoner, Argron. Journal, vol. 77:99–101, 1985.
Al–Niemi, T.S.; Campbell, W.F.; and M.D. Rumbaugh, Crop Sci. 32:976–980, 1992.
Rumbaugh, M.D., Johnson, and D.A., Pendery, Corp Sci. 33:1046–1050, 1993.
SokaL, R.R and F.J. Rohlf, Introduction to Biostatistics, W.H. Freeman and Comapny, N.Y., p. 333, 1987.
P.D. Walton, Principles and Practices of Plant Science, Prentice Hall, Englewood Cliffs, N.J., pp. 320–323, 1988.
Briggs et al. pp. 180, 196–211, 240–250 In: Introduction to Plant Breeding, Reinhold Publication Corp.: New York, 1967.

*Primary Examiner*—David T. Fox
*Assistant Examiner*—Anne Marie Grunberg
*Attorney, Agent, or Firm*—Hovey, Williams, Timmons & Collins

[57] ABSTRACT

Improved salt tolerant cultivars of alfalfa (*Medicago sativa* L.) are provided having enhanced germination and plant vigor properties in saline soil conditions. The preferred cultivars, ZS-9491 (ATCC 209015) and ZS-9592 (ATCC 209014), were derived from a cross of known alfalfa germplasms with subsequent recurrent selection for pre- and post-germination viability.

5 Claims, No Drawings

SALT TOLERANT ALFALFA

BACKGROUND OF THE INVENTION

1. Field of the Invention

The present invention is broadly concerned with improved salt tolerant alfalfa cultivars. More particularly, the invention pertains to novel field selected cultivars of *Medicago sativa* L. which exhibit enhanced germination and plant vigor when grown in salty soils.

2. Description of the Prior Art

Alfalfa (*Medicago sativa* L., also known as lucerne) is one of the world's most valuable forage legumes. It is grown for hay, pasture and silage, and is valued highly as a livestock feed. Alfalfa originated in the Near East, in the area extending from Turkey to Iran and north into the Caucasus. From the great diversity of forms within the genus Medicago, two species, *M. sativa* and *M. falcata*, have become important forage plants. These species are mainly tetraploid, with 32 chromosomes, although diploid forms are known. Alfalfa species are composed of ecotypes, population complexes adapted to the environment of a given climatic region or to definite habitats within a region.

Alfalfa is a herbaceous perennial legume characterized by a deep tap root showing varying degrees of branching. Erect or semi-erect stems, bearing an abundance of leaves, grow to a height of 2–3 feet. The number of stems arising from a single woody crown may vary from just a few to 50 or more. New stems develop when older ones mature or have been cut or grazed. Flowers are borne on axillary racemes which vary greatly in size and number of flowers. Flower color is predominantly purple, or bluish-purple, but other colors occur. The fruit is a legume, or pod, usually spirally coiled in *M. sativa*. Seeds are small, with about 220,000/lb., and the color varies from yellow to brown. Alfalfa is widely adapted to temperature and soil conditions, save for humid tropical conditions. Reproduction in alfalfa is mainly by cross-fertilization, but substantial self-pollination may also occur. Cross-pollination is effected largely by bees.

The commercial production of seeds for growing alfalfa plants normally involves four stages, the production of breeder, foundation, certified and registered seeds. Breeder seed is the initial increase of seed of the strain which is developed by the breeder and from which foundation seed is derived. Foundation seed is the second generation of seed increase and from which certified seed is derived. Certified seeds are used in commercial crop production and are produced from foundation or certified seed. Foundation seed normally is distributed by growers or seedsmen as planting stock for the production of certified seed.

Although alfalfa production is widely distributed, essentially all commercially available cultivars have very poor salt tolerance. As a consequence, it is very difficult to achieve adequate alfalfa yields (or even stands) in salty soil found in areas such as Southern California, Arizona, New Mexico and Texas. Salt tolerant varieties have heretofore not been available on the commercial market. Certain salt tolerant germplasm releases have been made which are useful in variety development. One such prior germplasm release, AZ-Germ Salt II was a laboratory development and has been noted for its ability to germinate in saline environments.

There is accordingly a real and unsatisfied need in the art for improved salt tolerant alfalfa cultivars which have the necessary degree of germination capacity and post-germination vigor which will make it possible to extend substantial alfalfa production to high salt soils.

SUMMARY OF THE INVENTION

The present invention overcomes the problems outlined above and provides salt tolerant alfalfa plant seeds and plants grown therefrom. Broadly speaking, the new cultivar seeds of the invention are sufficiently salt tolerant such that, when subjected to an aqueous germination environment comprising at least about 2.4% by weight salt (more preferably at least about 2.5% by weight salt), the seeds exhibit at least about a 50% germination rate. The germination test to be used in ascertaining this germination rate is a standard, art-recognized test entitled "Salt Tolerance of Germinating Alfalfa Seeds" described in the March, 1991 Edition of *Standard Tests to Characterize Alfalfa Cultivars*, published by the North American Alfalfa Improvement Conference, which is incorporated by reference herein.

In preferred forms, the salt tolerant alfalfa plant seeds have a lineage which includes *Medicago sativa* L. cultivar AZ-Germ Salt II; most preferably, the plant seeds also are descended from *Medicago sativa* L. cultivar AZ-90NDC-ST. The most preferred cultivars are referred to as ZS-949 1 and ZS-9592.

DETAILED DESCRIPTION OF THE PREFERRED EMBODIMENT

The cultivars of the present invention are descendants of a known salt-resistant germplasm, AZ-Germ Salt II, and a germplasm exhibiting increased forage yield under salt stress, AZ-90NDC-ST. The AZ-Germ Salt II germplasm (*Medicago sativa* L.), Reg. No. GP-212 (PI524968) was released in July 1988 and represents the ninth cycle of recurrent mass selection for alfalfa genotypes that germinate at high salt levels. AZ-90NDC-ST (*Medicago sativa* L., Reg. No. GP-241, PI545592) was released in August, 1990 as a broad-based, non-dormant, alfalfa germplasm exhibiting superior forage production in greenhouse trials under conditions of moderate salt stress. The registration descriptions for these cultivars are found in *Crop Science*, Vol. 29, p. 493 (1989) and *Crop Science*, Vol. 31, p. 1098 (1991), which are incorporated by reference herein.

ZS-9491 resulted from a cross of AZ-Germ Salt II and AZ-90NDC-ST with conventional post-germination selection for plant vigor. The initial crossed population was subjected to two cycles of selection for vigor and post-germination performance with increasing salinity conditions. A final cycle was performed with simultaneous selection for vigor, germination and forage production. During this process, some germination salt tolerance was lost initially, but was regained by the last cycle. The seed resulting from the three selection cycles was then used in a conventional field isolation technique to generate Breeder Seed. A portion of the Breeder Seed was then used to generate Foundation Seed used in salt tolerance tests. ZS-9592 is a single selection for forage production from ZS-9491 Foundation Seed. The ZS-9491 Breeder Seed and ZS-9592 seed have been deposited with the American Type Culture Collection (ATCC, Rockville, Md.) and have been accorded ATCC Accession Nos. 209015 and 209014, respectively.

The breeding methods used in accordance with the invention include, for example, methods described in Knowles et al., *Introduction to Plant Breeding* (Reinhold Publication Corp., New York, N.Y., 1967), incorporated by reference. In each successive cycle of increasing salt stress, selections were made on the basis of plant vigor and forage production.

EXAMPLE 1

In this example, the salt tolerance of cultivars in accordance with the invention were tested, as compared with standardized salt resistant and salt susceptible cultivars, and against five commercially available varieties. The salt tolerance test performed was the standard test "Salt Tolerance of Germinating Alfalfa Seeds", described in the March, 1991 Edition of *Standard Tests to Characterize Alfalfa Cultivars*. Briefly, however, scarified test seeds not previously treated with fungicides or inoculated were germinated in solution plates each containing 4.5 ml of a different concentration of sodium chloride in water (25 seeds per plate, 2 replications): 0.00, 0.50, 0.75, 1.00, 1.25, 1.50, 1.75 and 2.00 percent (w/w). Germinated and hard seeds were counted after seven days time. Germination in each plate was computed by subtracting the number of hard seeds from 25 to obtain a corrected total, and the number of germinated seeds was divided by the corrected total to obtain the fraction germinated. Further calculations generated the predicted salt concentration needed to reduce the germination of each cultivar to 50% and 75%.

The following data sets forth the results of this salt tolerance test:

TABLE 1

| Cultivar | % Salt to Reduce Germination to 50% | Confidence Interval (95%) | % Salt to Reduce Germination to 75% | Confidence Interval (95%) |
|---|---|---|---|---|
| AZ-Germ Salt II[1] | 3.57 | 2.46–20.79 | 2.42 | 1.79–10.9 |
| ZS-9491 | 2.64 | 2.18–18.51 | 2.27 | 1.95–10.15 |
| ZS-9592 | 2.58 | 2.15–4.31 | 2.06 | 1.78–2.98 |
| Commercial Seed A | 2.12 | 1.84–2.70 | 1.56 | 1.35–1.84 |
| Commercial Seed B | 1.74 | 1.56–2.00 | 1.49 | 1.37–1.59 |
| Commercial Seed C | 1.70 | 161–1.83 | 1.43 | 1.30–1.54 |
| Commercial Seed D | 1.69 | 1.47–2.04 | 1.28 | 1.09–1.44 |
| Commercial Seed E | 1.67 | 1.56–1.79 | 1.08 | 0.83–1.29 |
| Mesa Sirsa | 1.15 | 1.03–1.27 | 0.83 | 0.66–0.96 |
| Malone | 1.11 | 0.98–1.24 | 0.75 | 0.56–0.89 |
| Saranac[2] | 0.85 | 0.71–0.97 | 0.53 | 0.33–0.67 |

[1]The salt resistant check standard seed.
[2]The salt susceptible standard seed.

The ZS-9491 and ZS-9592 cultivars are very tolerant to salt, and the level of resistance is comparable to the resistant check cultivar AZ-Germ Salt II. The latter cultivar was developed under stringent laboratory conditions solely for germination in high salt concentrations. However, the ZS-9491 and ZS-9592 cultivars are more agronomically desirable than AZ-Germ Salt II because the final selections of the cultivars of the invention were made in the field and not under controlled laboratory conditions.

EXAMPLE 2

In this example, the salt-tolerant cultivars of the invention were tested in grower fields in El Centro, Calif. The content of soluble salts in the El Centro grower field measured 0.6–2.7 mmhos/cm, and the pH ranged between 7.5 and 8.1. The soil contained predominately sandy clay loam. Because the fields contained sandy soil, Phytophthora root rot did not limit production. Three forage harvests were completed at the El Centro location. The amount of forage in pounds of dry matter after the three harvests of ZS 9592 and ZS 9491 were compared against that of forty-six other alfalfa varieties. The first cut was eliminated from the data because aphid pressure caused a high CV level (30%). However, ZS 9491 and ZS 9592 ranked #1 and #2, respectively, in the trial for forage material, with average yields of 3.33 lbs/dry matter and 3.18 lbs/dry matter. In the second cut, ZS 9592 ranked first with an average of 8.57 lbs/dry matter and ZS 9491 ranked fourth with 7.73 lbs/dry matter. (See Table 2). ZS 9592 also ranked first in the third cut averaging 7.7 lbs/dry matter whereas ZS 9491 ranked nineteenth with 7.05 lbs/dry matter. (See Table 3).

TABLE 2

Average Forage Yield Data
El Centro, California

| Alfalfa Variety | Cut #2 Average Yield (Lbs/Dry Matter) |
|---|---|
| ZS 9592 | 8.57 |
| Comparative Strain #1 | 8.03 |
| Comparative Strain #2 | 7.90 |
| Comparative Strain #3 | 7.73 |
| ZS 9491 | 7.73 |
| Comparative Strain #4 | 7.66 |
| Comparative Strain #5 | 7.65 |

TABLE 2-continued

Average Forage Yield Data
El Centro, California

| Alfalfa Variety | Cut #2 Average Yield (Lbs/Dry Matter) |
|---|---|
| Comparative Strain #6 | 7.58 |
| Comparative Strain #7 | 7.58 |
| Comparative Strain #8 | 7.48 |
| Comparative Strain #9 | 7.43 |
| Comparative Strain #10 | 7.40 |
| Comparative Strain #11 | 7.38 |
| Comparative Strain #12 | 7.35 |
| Comparative Strain #13 | 7.30 |
| Comparative Strain #14 | 7.23 |
| Comparative Strain #15 | 7.23 |
| Comparative Strain #16 | 7.17 |
| Comparative Strain #17 | 7.13 |
| Comparative Strain #18 | 7.13 |
| Comparative Strain #19 | 7.08 |
| Comparative Strain #20 | 7.05 |
| Comparative Strain #21 | 7.03 |
| Comparative Strain #22 | 7.00 |
| Comparative Strain #23 | 6.95 |
| Comparative Strain #24 | 6.93 |
| Comparative Strain #25 | 6.90 |
| Comparative Strain #26 | 6.85 |
| Comparative Strain #27 | 6.83 |
| Comparative Strain #28 | 6.83 |
| Comparative Strain #29 | 6.80 |

TABLE 2-continued

Average Forage Yield Data
El Centro, California

| Alfalfa Variety | Cut #2 Average Yield (Lbs/Dry Matter) |
| --- | --- |
| Comparative Strain #30 | 6.68 |
| Comparative Strain #31 | 6.50 |
| Comparative Strain #32 | 6.50 |
| Comparative Strain #33 | 6.45 |
| Comparative Strain #34 | 6.40 |
| Comparative Strain #35 | 6.23 |
| Comparative Strain #36 | 6.20 |
| Comparative Strain #37 | 6.18 |
| Comparative Strain #38 | 6.08 |
| Comparative Strain #39 | 5.80 |
| Comparative Strain #40 | 5.80 |
| Comparative Strain #41 | 5.50 |
| Comparative Strain #42 | 5.48 |
| Comparative Strain #43 | 5.43 |
| Comparative Strain #44 | 5.35 |
| Comparative Strain #45 | 5.23 |
| Comparative Strain #46 | 4.85 |

TABLE 3

Average Forage Yield Data
El Centro, California

| Alfalfa Variety | Cut #3 Average Yield (Lbs/Dry Matter) |
| --- | --- |
| ZS 9592 | 7.77 |
| Comparative Strain #1 | 7.70 |
| Comparative Strain #20 | 7.63 |
| Comparative Strain #4 | 7.45 |
| Comparative Strain #12 | 7.35 |
| Comparative Strain #2 | 7.35 |
| Comparative Strain #14 | 7.33 |
| Comparative Strain #15 | 7.30 |
| Comparative Strain #6 | 7.28 |
| Comparative Strain #11 | 7.26 |
| Comparative Strain #8 | 7.23 |
| Comparative Strain #18 | 7.23 |
| Comparative Strain #10 | 7.18 |
| Comparative Strain #28 | 7.13 |
| Comparative Strain #29 | 7.13 |
| Comparative Strain #9 | 7.13 |
| Comparative Strain #24 | 7.10 |
| Comparative Strain #40 | 7.10 |
| ZS 9491 | 7.05 |
| Comparative Strain #5 | 7.05 |
| Comparative Strain #21 | 7.00 |
| Comparative Strain #12 | 7.00 |
| Comparative Strain #7 | 6.90 |
| Comparative Strain #27 | 6.90 |
| Comparative Strain #17 | 6.83 |
| Comparative Strain #13 | 6.83 |
| Comparative Strain #25 | 6.80 |
| Comparative Strain #16 | 6.80 |
| Comparative Strain #19 | 6.63 |
| Comparative Strain #26 | 6.63 |
| Comparative Strain #23 | 6.58 |
| Comparative Strain #36 | 6.55 |
| Comparative Strain #3 | 6.48 |
| Comparative Strain #34 | 6.48 |
| Comparative Strain #30 | 6.43 |
| Comparative Strain #35 | 6.18 |
| Comparative Strain #22 | 6.13 |
| Comparative Strain #31 | 6.07 |
| Comparative Strain #43 | 6.03 |
| Comparative Strain #42 | 5.98 |
| Comparative Strain #45 | 5.78 |
| Comparative Strain #37 | 5.78 |
| Comparative Strain #41 | 5.77 |
| Comparative Strain #33 | 5.73 |
| Comparative Strain #44 | 5.70 |
| Comparative Strain #39 | 5.25 |
| Comparative Strain #46 | 5.00 |

Thus, ZS 9592 demonstrated the highest productivity of all forty-eight alfalfa varieties participating in the grower field trials, and ZS 9491 also showed a significantly higher level of productivity than the majority of the other alfalfa varieties. Accordingly, the salt-tolerant cultivars will also do well in areas where soil salt content is negligible for most crops or restricts the yields of some salt-sensitive crops in addition to succeeding in high salt concentration soils.

EXAMPLE 3

A 25-acre field in Calipatria, Calif. having a soluble salt electrical conductivity of 32.2 mmhos/cm was seeded with ZS 9491. The first cut from this field produced 534 bales, with bales averaging 125 pounds each. Prior attempts to grow alfalfa in this field had failed.

Accordingly, the salt-tolerant cultivars of the invention will do well in areas where salt is a limiting factor in alfalfa production, especially in areas where the farmer is growing alfalfa but experiences yield reductions owing to salt in the soil or irrigation water, or where difficulty is experienced in getting an alfalfa stand due to salt. The cultivars hereof should be used in areas where phytophthora is not known to cause severe crop damage. This disease is common in heavy soils in the central valley of California where the concentration of salt in the soil and irrigation waters is low. However, in areas where salt is the main limiting growth factor, phytophthora root rot may be adversely affected by the salt and therefore the disease may not be as severe.

The cultivars of the invention should be particularly useful in sandy soils in Southern California, Arizona, New Mexico and Texas where salt is a factor. The cultivars have high resistance to the Southern Root Knot Nematode that is prevalent in these soils. Such nematode resistance, as well as resistance to the Blue Alfalfa Aphid, render the cultivars especially attractive for these locales.

It is claimed:

1. An alfalfa plant seed selected from the group consisting of ATCC No. 209015 and ATCC No. 209014.

2. The alfalfa seed of claim 1, said seed, when subjected to an aqueous germination environment comprising at least about 2.0% sodium chloride by weight, exhibiting at least about a 50% germination rate.

3. An alfalfa plant grown from a seed of claim 1.

4. An alfalfa seed descended from a seed selected from the group consisting of ATCC No. 209015 and ATCC No. 209014. wherein said alfalfa seed has all the identifying characteristics of ATCC No. 209015 or ATCC No. 209014.

5. The alfalfa seed of claim 4, said seed, when subjected to an aqueous germination environment comprising at least about 2.0% sodium chloride by weight, exhibiting at least about a 50% germination rate.

* * * * *